US012653591B2

(12) United States Patent
Varner et al.

(10) Patent No.: US 12,653,591 B2
(45) Date of Patent: Jun. 16, 2026

(54) DIFFERENTIAL COMPRESSION BONE SCREW

(71) Applicant: In2Bones USA, LLC, Memphis, TN (US)

(72) Inventors: Kevin E. Varner, Memphis, TN (US); Keith A. Heier, Memphis, TN (US); Travis W. Hanson, Memphis, TN (US); Casey M. Chambers, Memphis, TN (US); Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 206 days.

(21) Appl. No.: 18/401,004

(22) Filed: Dec. 29, 2023

(65) Prior Publication Data

US 2024/0130769 A1 Apr. 25, 2024

Related U.S. Application Data

(63) Continuation of application No. 17/319,567, filed on May 13, 2021, now Pat. No. 11,857,235, which is a continuation of application No. 16/422,141, filed on May 24, 2019, now Pat. No. 11,020,159, which is a continuation of application No. 15/612,520, filed on Jun. 2, 2017, now Pat. No. 10,349,992.

(60) Provisional application No. 62/344,823, filed on Jun. 2, 2016.

(51) Int. Cl.
*A61B 17/86* (2006.01)
*A61B 17/80* (2006.01)

(52) U.S. Cl.
CPC .......... *A61B 17/863* (2013.01); *A61B 17/809* (2013.01); *A61B 17/8605* (2013.01); *A61B 17/80* (2013.01); *A61B 17/8635* (2013.01)

(58) Field of Classification Search
CPC ........................... A61B 17/863; A61B 17/809
See application file for complete search history.

(56) References Cited

U.S. PATENT DOCUMENTS

| | | | | |
|---|---|---|---|---|
| 10,130,407 | B2 * | 11/2018 | Castaneda | .......... A61B 17/8888 |
| 10,349,992 | B2 * | 7/2019 | Varner | .............. A61B 17/8605 |
| 2004/0098045 | A1 * | 5/2004 | Grafton | .............. A61B 17/0401 |
| | | | | 606/213 |

* cited by examiner

*Primary Examiner* — Christian A Sevilla
(74) *Attorney, Agent, or Firm* — Rutan & Tucker LLP; Hani Z. Sayed

(57) ABSTRACT

A differential compression bone screw and a method are provided for compressing adjacent bone portions together to encourage bone fusion. The compression bone screw is comprised of a head portion and a shank. A center hole extends from the head portion to a distal end of the shank. A superior end of the head portion includes a shaped opening that receives a tool for driving the compression bone screw into a hole drilled in a patient's bone. An inferior end of the head portion includes barbs that engage with surrounding bone tissue. A smooth portion of the shank is disposed between proximal threads and distal threads that rotatably engage within the hole in the patient's bone. A thread pitch of the distal threads is greater than a thread pitch of the proximal threads, such that the compression bone screw comprises a differential pitch configured to compress the adjacent bone portions.

18 Claims, 4 Drawing Sheets

DIFFERENTIAL COMPRESSION BONE SCREW

PRIORITY

This application is a continuation of U.S. patent application Ser. No. 17/319,567 filed on May 13, 2021 and U.S. patent application Ser. No. 16/422,141 filed on May 24, 2019 and U.S. patent application Ser. No. 15/612,520, filed Jun. 2, 2017, now issued as U.S. Pat. No. 10,349,992 which claims the benefit of and priority to U.S. Provisional Application No. 62/344,823, filed Jun. 2, 2016, both entitled "Differential Compression Bone Screw", the entirety of which are incorporated herein by reference.

FIELD

The field of the present disclosure generally relates to securing bones together. More particularly, the field of the present disclosure relates to bone screws and methods for repairing bones of a patient.

BACKGROUND

A fusion bone plate implant may be utilized in conjunction with one or more fasteners so as to generate compression and stability at a bone interface. An implant coupled with fasteners generally serves to stabilize bones, or bone parts, relative to one another so as to promote bone fusion. In many applications, bone plates and fasteners are used to fuse bones, or bone parts, of the human body, such as bones in the foot, the ankle, the hand, the wrist, as well as various other portions of the body. Furthermore, during the course of certain medical procedures, a surgeon may immobilize one or more bones or the bone fragments by stabilizing the bones together in a configuration which approximates the natural anatomy. To this end, the surgeon may use fasteners to attach the bones to a bone plate implant so as to hold the bones in alignment with one another while they fuse together.

In some instances, however, a bone plate may be impractical for implantation in a portion of the body that requires treatment. What is needed, therefore, is a compression bone screw that is configured to fuse bones in absence of a fusion bone plate.

SUMMARY

A compression bone screw and a method are provided for compressing adjacent bone portions together. The compression bone screw is comprised of a head portion that includes a superior end and an inferior end. A shank extends distally from the inferior end to a distal end. Proximal threads and distal threads are disposed along the shank and are configured to rotatably engage within a hole drilled in a patient's bone. The proximal threads are comprised of a first thread pitch and the distal threads are comprised of a second thread pitch, such that the shank comprises a differential pitch. The second thread pitch is greater than the first thread pitch, such that engaging the screw within the hole causes the distal threads to push a first bone portion toward a second bone portion near the proximal threads, thereby closing a fracture between the first and second bone portions. Intermediate threads may be disposed between the distal and proximal threads and comprise a thread pitch that decreases from the second thread pitch near the distal threads to the first thread pitch near the proximal threads.

In an exemplary embodiment, a compression bone screw for compressing adjacent bone portions together comprises a head portion comprised of a superior end and an inferior end; a shank extending distally from the inferior end to a distal end; and proximal threads and distal threads disposed along the shank, the proximal threads comprised of a first thread pitch and the distal threads comprised of a second thread pitch, such that the shank comprises a differential pitch. In another exemplary embodiment, intermediate threads are disposed between the distal threads and the proximal threads and comprise a thread pitch that decreases from the second thread pitch near the distal threads to the first thread pitch near the proximal threads.

In another exemplary embodiment, a center hole extends from the head portion to the distal end and is configured to receive any of various guidewires, trocars, and other similar instruments configured to direct the compression bone screw to a target opening of a hole drilled in a bone. In another exemplary embodiment, the superior end includes a shaped opening that is substantially concentric with the head portion and configured to engagedly receive a tool for driving the compression bone screw into the hole drilled in the bone, and wherein the inferior end comprises a plurality of barbs disposed around the circumference of the inferior end and configured to fixedly engage with surrounding bone tissue. In another exemplary embodiment, the inferior end is configured to engage within an opening of the hole drilled in the bone, such that the superior end countersinks below the exterior surface of the bone. In another exemplary embodiment, the inferior end is configured to engage within an opening of a bone fusion plate, such that the superior end countersinks within the opening and the inferior end presses the bone fusion plate against the surface of the bone.

In another exemplary embodiment, the distal threads and the proximal threads are configured to rotatably engage within a hole drilled in a bone, such that the compression bone screw advances into the hole upon being turned by way of a suitable tool. In another exemplary embodiment, the proximal threads comprise a first diameter, the distal threads comprise a second diameter, and a smooth portion disposed between the proximal threads and the distal threads is comprised of a diameter that is less than the first diameter and the second diameter, and wherein the first diameter is greater than the second diameter. In another exemplary embodiment, a tapered diameter extends from the second diameter to a rounded portion comprising the distal end, the rounded portion and the tapered diameter being configured to minimize resistance to forward movement of the compression bone screw advancing within the interior of a hole drilled in a bone. In another exemplary embodiment, one or more flutes are disposed along the tapered diameter and comprised of at least one cutting edge configured to clean the interior of a hole drilled in a bone during advancing of the compression bone screw within the hole.

In another exemplary embodiment, the second thread pitch is greater than the first thread pitch, such that the distal threads push a first bone portion toward a second bone portion near the proximal threads, thereby closing a fracture between the first bone portion and the second bone portion. In another exemplary embodiment, a smooth portion disposed between the proximal threads and distal threads is configured to allow the fracture to close as the first bone portion and the second bone portion are compressed together. In another exemplary embodiment, the second thread pitch ranges between substantially 1-3 times greater than the first thread pitch. In another exemplary embodiment, the second thread pitch is substantially 2-times greater than the first thread pitch. In another exemplary embodiment, intermediate threads are disposed between the distal threads and the proximal threads, the intermediate threads having a thread pitch that decreases from the second thread pitch near the distal threads to the first thread pitch near the proximal threads.

In an exemplary embodiment, a method for a differential compression bone screw comprises forming a head portion comprised of a superior end and an inferior end; orienting a shank distally from the inferior end; and configuring a differential thread pitch along the shank. In another exemplary embodiment, configuring the differential thread pitch comprises configuring proximal threads having a first thread pitch and configuring distal threads having a second thread pitch, such that the second thread pitch is greater than the first thread pitch. In another exemplary embodiment, configuring the differential thread pitch further comprises disposing intermediate threads between the distal threads and the proximal threads, the intermediate threads having a thread pitch that decreases from the second thread pitch near the distal threads to the first thread pitch near the proximal threads. In another exemplary embodiment, configuring the differential thread pitch further comprises forming a smooth portion of the shank disposed between the proximal threads and the distal threads. In another exemplary embodiment, orienting the shank further comprises extending a center hole from the head portion to a distal end of the shank and surrounding the center hole with a shaped opening in the superior end. In another exemplary embodiment, forming the head portion further comprises configuring a plurality of barbs disposed around the circumference of the inferior end so as to fixedly engage with surrounding bone tissue.

BRIEF DESCRIPTION OF THE DRAWINGS

The drawings refer to embodiments of the present disclosure in which.

Figure 1:
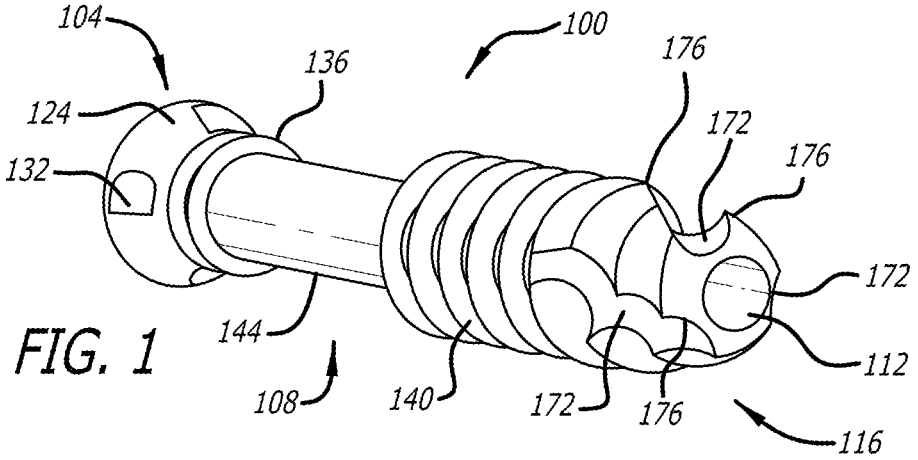
FIG. 1 illustrates an isometric view of a distal portion of an exemplary embodiment of a compression bone screw that may be used for repairing bones of a patient.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first screw," may be made. However, the specific numeric reference should not be interpreted as a literal sequential order but rather interpreted that the "first screw" is different than a "second screw." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus and a method for a differential compression bone screw for compressing two adjacent bone portions together, including compressing bone fractures, fixating osteotomies, and joining fusions. The compression bone screw is comprised of a head portion and a distally extending shank. A center hole extends from the head portion to a distal end of the shank. The head portion is comprised of a superior end and an inferior end. The superior end includes a shaped opening that is substantially concentric with the center hole and configured to engagedly receive a tool for driving the compression bone screw into a hole drilled in a patient's bone. The inferior end includes a plurality of barbs that are disposed around the circumference of the inferior end and are configured to fixedly engage with surrounding bone tissue. Proximal threads and distal threads are disposed on the shank and configured to rotatably engage within the hole in the patient's bone, such that the compression bone screw advances into the hole upon being turned by way of the tool. A thread pitch of the distal threads preferably is greater than a thread pitch of the proximal threads, such that the compression bone screw comprises a differential pitch configured to compress the two adjacent bone portions, thereby closing a fracture there between.

Figure 2:
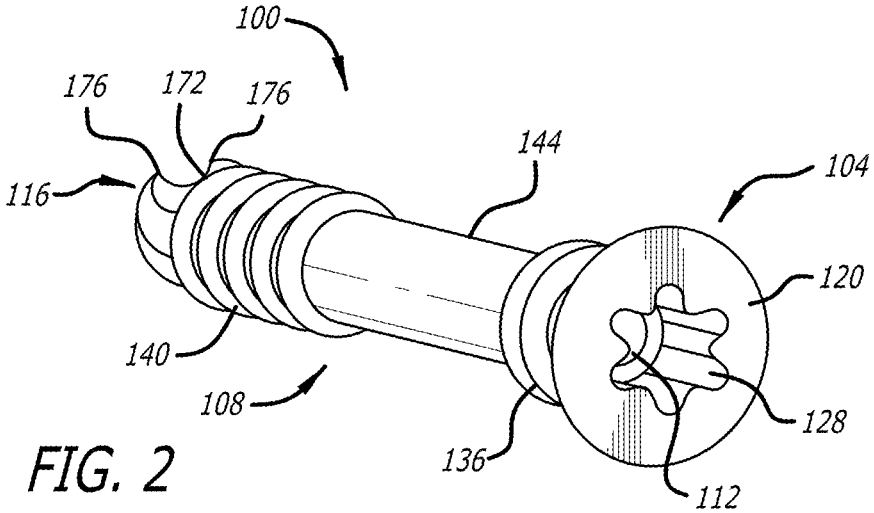
FIG. 2 illustrates an isometric view of a proximal portion of an exemplary embodiment of a compression bone screw that may be used for repairing bones of a patient.

FIGS. 1-4 illustrate an exemplary embodiment of a compression bone screw 100 that may be used for repairing bone fractures, fixating osteotomies, joining fusions of the skeletal system, and the like. It should be understood that the terms "bone screw," "fastener," "fixator," "elongate member," and "screw" may be used interchangeably herein as they essentially describe the same type of device. The compression bone screw 100 generally is an elongate member comprised of a head portion 104 and a shank 108. As best shown in FIGS. 1-2, a cannulation or center hole 112 extends longitudinally from the head portion 104 to a distal end 116 of the shank 108. The center hole 112 is configured to receive any of various guidewires, trocars, and other similar instruments for directing the bone screw to a hole drilled in the patient's bone.

The head portion 104 is comprised of a superior end 120 and an inferior end 124. As best illustrated in FIG. 2, the superior end 120 may include a shaped opening 128 that is substantially concentric with the center hole 112. The shaped opening 128 generally is configured to engagedly receive a tool suitable for driving the bone screw 100 into the hole drilled in the patient's bone. Although in the illustrated embodiment, the shaped opening 128 is comprised of a hexalobe shape, any of various multi-lobe shapes, as well as other polygonal shapes, are also contemplated.

The inferior end 124 preferably is configured to countersink within the hole in the bone. Thus, the superior end 120 is not left protruding above the exterior surface of the bone once the compression bone screw 100 is fully engaged with the patient's bone. Further, a plurality of barbs 132 disposed around the circumference of the inferior end 124 are configured to engage with the surrounding bone tissue so as to prevent the bone screw from backing out of the hole in the patient's bone. In some embodiments, however, the inferior end 124 may be configured to be received within an opening of a bone fusion plate, such that the superior end 120 countersinks within the opening of the bone fusion plate and presses the plate against the surface of the patient's bone.

Figure 3:
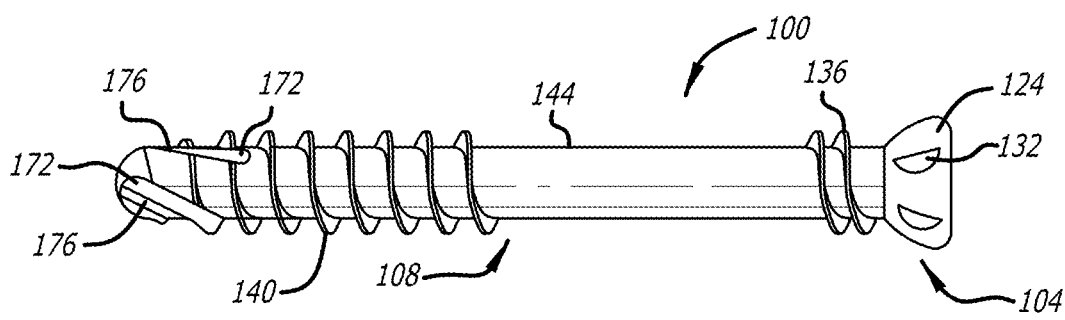
FIG. 3 illustrates a side view of an exemplary embodiment of a compression bone screw that may be used for repairing bones of a patient.
Figure 4:
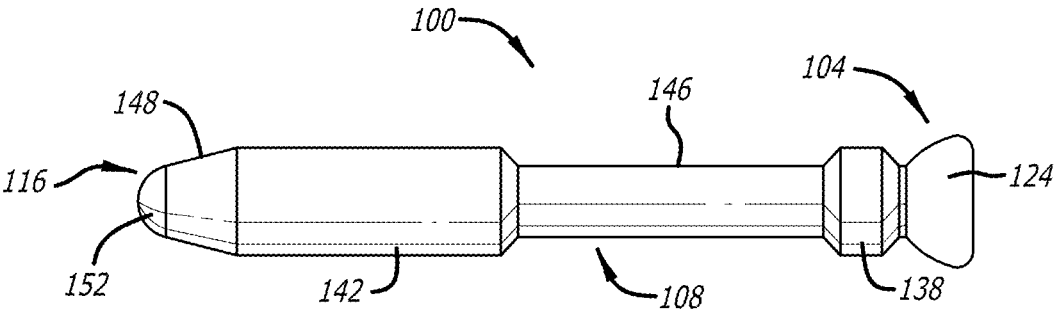
FIG. 4 illustrates a side view of the exemplary embodiment of the compression bone screw of FIG. 3, showing exterior diameters along a shank of the compression bone screw.

As best shown in FIGS. 3-4, the shank 108 is comprised of proximal threads 136 and distal threads 140 that share an intervening smooth portion 144. The proximal threads 136 have a diameter 138, and the distal threads 140 have a diameter 142. A tapered diameter 148 extends from the distal threads 140 to a rounded portion 152 that comprises the distal end 116. The smooth portion 144 is comprised of a diameter 146 that is less than the diameters 138 and 142 so as to facilitate passing the smooth portion 144 through the bone with relatively little resistance. Further, in the illustrated embodiment, the threads 136 and 140 share substantially similar exterior diameters, 138 and 142, respectively, as shown in FIG. 4. In some embodiments, however, the diameter 138 of the proximal threads 136 may be greater than the diameter 142 of the distal threads 140. Various diameters of the proximal threads 136 and the distal threads 140, as well as the diameter 146, are contemplated, without limitation.

The threads 136 and 140 are configured to rotatably engage within a suitably sized hole drilled in the patient's bone. Thus, turning the bone screw 100 in an appropriate direction by way of a tool coupled with the shaped opening 128, drives the distal threads 140 to engage with bone tissue surrounding the hole, and thus advancing the bone screw 100 deeper into the hole in the bone. The proximal threads 136 engage the bone once a majority of the bone screw 100 is already disposed within the hole in the bone. Continued turning of the bone screw 100 then countersinks the inferior end 124 into an upper-most portion of the hole in the bone, and draws the superior end 120 beneath the exterior surface of the patient's bone.

Moreover, the illustrated embodiment of the compression bone screw 100 comprises a differential pitch wherein the distal threads 140 have a thread pitch that is greater than the thread pitch of the proximal threads 136. In operation, the greater thread pitch of the distal threads 140 pushes the bone portion near the distal threads toward the bone portion near the proximal threads 136. The diameter 146 of the smooth portion 144 allows the fracture to close as the bone portions are compressed together. In some embodiments, the thread pitch of the distal threads 140 may range between substantially 1-3 times greater than the thread pitch of the proximal threads 136. Preferably, however, the thread pitch of the distal threads 140 is substantially 2-times greater than the thread pitch of the proximal threads 136. A wide variety of differential pitch configurations are contemplated within the scope of the present disclosure.

Figure 5:
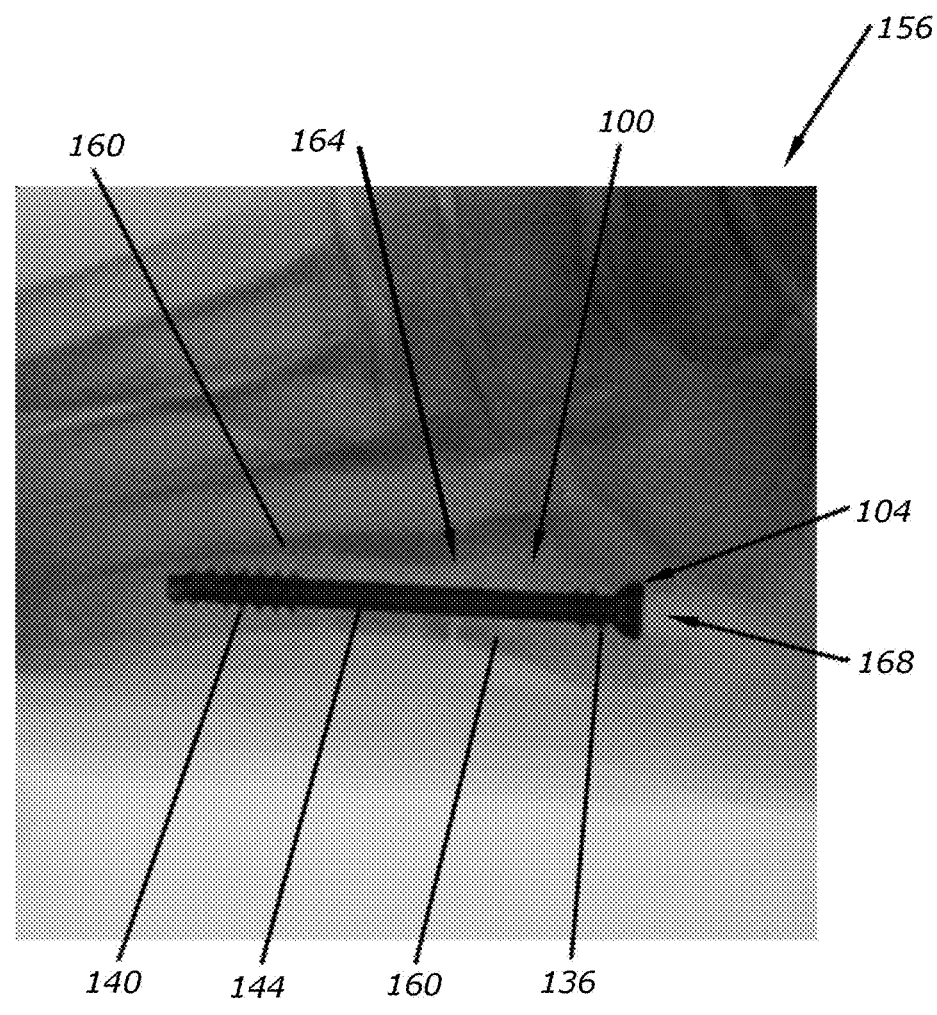
FIG. 5 illustrates an exemplary use environment wherein an exemplary embodiment of a differential compression bone screw is longitudinally disposed within substantially the center of a repaired bone.

It is contemplated that the differential pitch of the compression bone screw 100 is particularly well suited for compressing bone fractures, fixating osteotomies, joining fusions, as well as any other surgical procedure wherein compressing two adjacent bone portions is desired, without limitation. It is further contemplated that the compression bone screw 100 may be advantageously oriented longitudinally with respect to a patient's bone. FIG. 5 illustrates an exemplary use environment 156 wherein the compression bone screw 100 is longitudinally disposed within substantially the center of a repaired bone 160. The proximal threads 136 and the distal threads 140 are engaged with healthy bone tissue, while a repaired fracture 164 is disposed along the smooth portion 144. Further, the head portion 104 is countersunk within an entry hole 168 that was drilled into the repaired bone 160 by a surgeon. As will be appreciated, the compression bone screw 100 may be implemented in any of various lengths and diameters so as to advantageously repair a wide variety of differently sized and shaped bones within the human body. Furthermore, it is envisioned that the compression bone screw 100 may be configured for use in a veterinary capacity, and thus the bone screw 100 may be implemented with various shapes and sizes that are suitable for use in different types of animals.

As will be appreciated, the rounded portion 152 and the tapered diameter 148 are configured to minimize resistance to forward movement of the compression bone screw 100 advancing within the interior of a bone hole. As best shown in FIG. 1, the distal end 116 and the tapered diameter 148 of the bone screw 100 are further comprised of one or more flutes 172 that extend from adjacent of the center hole 112 and spiral along the tapered diameter 148. A pair of cutting edges 176 borders each of the flutes 172. Although the illustrated embodiment of the bone screw 100 comprises three flutes 172, and thus six cutting edges 176, more than or less than three flutes 172 and six cutting edges 176 may be incorporated into different implementations of the bone screw 100 without limitation. As will be appreciated, the cutting edges 176 advantageously clean the interior of the bone hole and increase the diameter of the hole to accept the distal threads 140 of the advancing bone screw 100. As will be appreciated, the spiral, or a rate of twist, of the flutes 172 generally controls the rate of bone debris removal from the interior of the bone hole during rotation of the bone screw 100. It is contemplated that the flutes 172 may be implemented with any of various spirals without deviating beyond the spirit and scope of the present disclosure.

Figure 6:
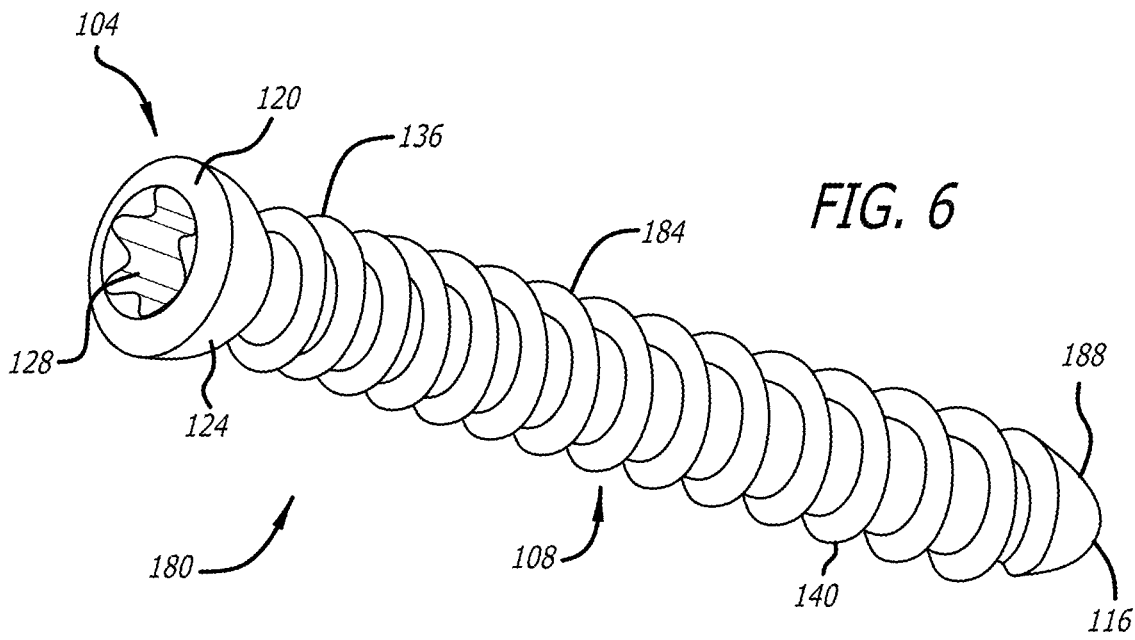
FIG. 6 illustrates an isometric view of a proximal portion of an exemplary embodiment of a compression bone screw that may be used for repairing bones of a patient.
Figure 7:
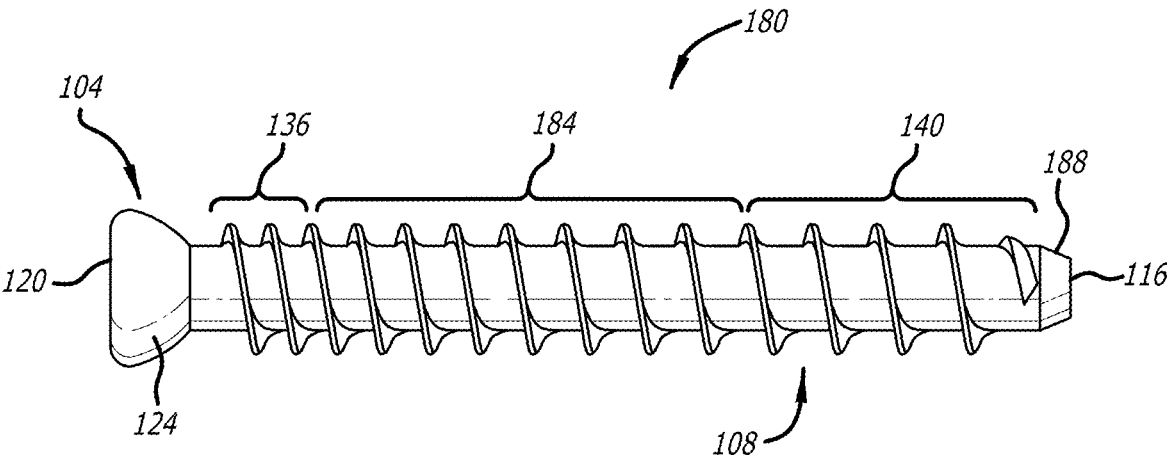
FIG. 7 illustrates a side view of the exemplary embodiment of the compression bone screw of FIG. 6, showing a differential thread pitch disposed along a shank of the compression bone screw.

FIGS. 6-7 illustrate an exemplary embodiment of a compression bone screw 180 that may be used for repairing bones of a patient. The compression bone screw 180 is substantially similar to the compression bone screw 100, illustrated in FIGS. 1-3, with the exception that the compression bone screw 180 is comprised of intermediate threads 184 in lieu of the smooth portion 144. As best shown in FIG. 7, the intermediate threads 184 extend from the distal threads 140 to the proximal threads 136, such that a continuous series of threads are disposed along substantially an entirety of the shank 108. Further, a tapered diameter 188 extends from the distal threads 140 to the distal end 116. The tapered diameter 188 and the distal end 116 are configured to minimize resistance to forward movement of the compression bone screw 180 advancing within the interior of a bone hole. It is contemplated that, in some embodiments, the tapered diameter 188 may be further comprised of one or more flutes 172 and cutting edges 176 that extend from the distal end 116 to the distal threads 140, as described herein.

The intermediate threads 184 may have a thread pitch that generally changes along the length of the shank 108. In the illustrated embodiment of FIGS. 6-7, the intermediate threads 184 have a thread pitch that continuously decreases from the thread pitch of the distal threads 140 to the relatively smaller thread pitch of the proximal threads 136. In some embodiments, the intermediate threads 184 may be comprised of a thread pitch near the distal threads 140 that ranges between substantially 1-3 times greater than the thread pitch of the intermediate threads that are near the proximal threads 136. In some embodiments, the intermediate threads 184 may be comprised of a thread pitch near the distal threads 140 that decreases from substantially 2-times greater than the thread pitch near the proximal threads 136. During operation of the compression bone screw 180, the greater thread pitch of the distal threads 140 and nearby intermediate threads 184 pushes the bone portion near the distal threads toward the bone portion near the proximal threads 136. As will be appreciated, during operation of the compression bone screw 180, the decreasing thread pitch of the intermediate threads 184 contributes to compressing the bone portion near the distal threads 140 toward the bone portion near the proximal threads 136. A wide variety of differential pitch configurations are contemplated within the scope of the present disclosure.

Moreover, in some embodiments, wherein the proximal threads 136 have a larger diameter than the distal threads 140, the intermediate threads 184 may be comprised of a diameter that continuously increases from the diameter of the distal threads 140 to the diameter of the proximal threads 136. In some embodiments, the intermediate threads 184 may have a diameter that is larger than the diameter of the distal threads 140 and is smaller than the diameter of the proximal threads 136. In still some embodiments, the diameter of the intermediate threads 184 may be substantially the same as the diameter of the distal threads 140 along a majority of the intermediate threads and then abruptly increase to match the diameter of the proximal threads 136. It should be understood, therefore, that a wide variety of relationships between the shapes and sizes of the distal threads 140, the intermediate threads 184, and the proximal threads 136 are contemplate and may be implemented within the spirit and the scope of the present disclosure.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:
1. A method for a bone compression screw, comprising:
    forming a shank having a head portion;
    extending a center hole through the head portion and the shank;

forming at least one barb on a tapered portion of the head portion; and
    forming threads along the shank;
    wherein forming the threads includes forming at least distal threads near a distal end of the shank and proximal threads near the head portion;
    wherein forming the threads includes arranging a differential pitch that comprises a distal thread pitch that is greater than a proximal thread pitch.

2. The method of claim 1, wherein arranging the differential pitch includes adapting the differential pitch for compressing bone fractures, fixating osteotomies, and joining fusions.

3. The method of claim 1, wherein arranging the differential pitch includes arranging the distal thread pitch to be between substantially 1 to 3 times greater than the proximal thread pitch.

4. The method of claim 3, wherein arranging the distal thread pitch comprises arranging the distal thread pitch to be substantially 2 times greater than the proximal thread pitch.

5. The method of claim 1, wherein arranging the differential pitch includes configuring the distal thread pitch to push a distal bone portion toward a proximal bone portion.

6. The method of claim 5, wherein forming the threads includes disposing a smooth portion between the distal threads and the proximal threads to allow the distal bone portion and the proximal bone portion to be compressed together.

7. The method of claim 1, wherein forming the threads includes forming intermediate threads between the distal threads and the proximal threads.

8. The method of claim 7, wherein forming the intermediate threads includes extending the intermediate threads from the distal threads to the proximal threads, such that a continuous series of threads is disposed along substantially an entirety of the shank.

9. The method of claim 8, wherein forming the intermediate threads includes arranging an intermediate thread pitch that changes along the length of the shank.

10. The method of claim 9, wherein forming the intermediate threads includes increasing the intermediate thread pitch from the proximal thread pitch to the distal thread pitch.

11. The method of claim 10, wherein forming the intermediate threads includes increasing the intermediate thread pitch from a first thread pitch that is substantially the same as the proximal thread pitch to a second thread pitch that ranges between substantially 1 to 3 times greater than the proximal thread pitch.

12. The method of claim 11, wherein forming the intermediate threads includes configuring the first thread pitch and the second thread pitch to cause the intermediate threads to contribute to compressing a distal bone portion against a proximal bone portion.

13. The method of claim 11, wherein forming the intermediate threads includes configuring the second thread pitch to be about 2 times greater than the first thread pitch.

14. The method of claim 1, wherein forming the shank includes tapering a diameter of the shank between the distal threads and the distal end of the shank.

15. The method of claim 14, wherein tapering the diameter includes adapting the distal end to minimize resistance to forward movement of the compression bone screw within a hole drilled in bone.

16. The method of claim 14, wherein tapering the diameter includes extending one or more flutes and cutting edges from the center hole to the distal threads.

17. The method of claim 16, wherein extending the one or more flutes and cutting edges includes bordering each of the one or more flutes with a pair of cutting edges.

18. The method of claim 17, wherein tapering the diameter includes extending three flutes and six cutting edges from the center hole to the distal threads.

\* \* \* \* \*